(12) United States Patent  (10) Patent No.: US 7,678,330 B2
Ostrovsky et al.  (45) Date of Patent: Mar. 16, 2010

(54) SYSTEM, METHOD AND APPARATUS FOR USE IN BLOOD TESTING THROUGH LUMINESCENCE

(76) Inventors: Aleksandr Ostrovsky, 51 Birch Ave., Richmond Hill, Ontario (CA) L4C 6C4; Mikhail Leibovski, 95 Spring Garden Ave., Toronto, Ontario (CA) M2N 3G4

(*) Notice: Subject to any disclaimer, the term of this patent is extended or adjusted under 35 U.S.C. 154(b) by 677 days.

(21) Appl. No.: 11/364,273

(22) Filed: Mar. 1, 2006

(65) Prior Publication Data

US 2007/0207058 A1  Sep. 6, 2007

(51) Int. Cl.
*G01N 35/02* (2006.01)
*G01N 35/10* (2006.01)
*G01N 21/76* (2006.01)

(52) U.S. Cl. .............. 422/64; 422/63; 422/67; 422/82.05; 436/43; 436/45; 436/49; 436/174; 436/177; 436/180; 356/218

(58) Field of Classification Search ............ None
See application file for complete search history.

(56) References Cited

U.S. PATENT DOCUMENTS

| | | | |
|---|---|---|---|
| 3,617,222 A | | 11/1971 | Matte |
| 3,679,312 A | | 7/1972 | Mansberg |
| 4,243,322 A | | 1/1981 | Ingalz |
| 5,266,209 A | | 11/1993 | Knight |
| 5,316,726 A | * | 5/1994 | Babson et al. ............ 422/65 |
| 5,422,075 A | | 6/1995 | Saito |
| 5,445,794 A | | 8/1995 | Wihlborg |
| 5,501,838 A | | 3/1996 | Ootani |
| 5,516,692 A | | 5/1996 | Berndt |
| 5,653,940 A | * | 8/1997 | Carey et al. ............ 422/52 |
| 5,827,478 A | | 10/1998 | Carey et al. |
| 6,071,748 A | | 6/2000 | Modlin |
| 6,335,166 B1 | | 1/2002 | Ammann |
| 6,518,068 B1 | | 2/2003 | Gambini |
| 6,605,213 B1 | | 8/2003 | Ammann |
| 6,656,428 B1 | * | 12/2003 | Bickoff et al. ............ 422/58 |

(Continued)

FOREIGN PATENT DOCUMENTS

EP  0 899 572 A  3/1999

(Continued)

*Primary Examiner*—P. Kathryn Wright
(74) *Attorney, Agent, or Firm*—Larson & Larson, P.A.; Frank Liebenow

(57) ABSTRACT

The present invention seeks to provide an express-control system for analyzing the compatibility of blood with other substances. The present invention relates to a system, method and apparatus for use in blood testing and more specifically, food intolerance testing through analysis of blood using luminescence. The present invention utilizes a blood testing system and apparatus, which includes a displacement assembly, a blood divider assembly, a reagent divider assembly, an electro-optical multiplier assembly and a central controller. A sample of blood is added to a corresponding one of a plurality of canisters containing a test substance. Thereafter a luminescent reagent is added and the plurality of canisters are moved in the blood testing apparatus until the canisters begin to luminese. The amount of luminescence is measured and analyzed an indicator of compatibility of the blood with the test substance and more specifically as an indicator of the presence and activity of neutrophil in the blood and more specifically the granulacy of the blood.

15 Claims, 5 Drawing Sheets

U.S. PATENT DOCUMENTS

| | | |
|---|---|---|
| 2003/0092194 A1 | 5/2003 | Gambini |
| 2003/0148536 A1 | 8/2003 | Liang |
| 2006/0292038 A1* | 12/2006 | Johansson et al. ........ 422/82.05 |

FOREIGN PATENT DOCUMENTS

| | | |
|---|---|---|
| WO | WO 93/03347 A | 2/1993 |
| WO | WO 01/11374 A | 2/2001 |
| WO | WO 02/37078 A | 5/2002 |
| WO | WO 2004/072652 A | 8/2004 |

* cited by examiner

SYSTEM, METHOD AND APPARATUS FOR USE IN BLOOD TESTING THROUGH LUMINESCENCE

FIELD OF THE INVENTION

The present invention relates to a system, apparatus and method for use in blood testing and more specifically, food intolerance testing through analysis of blood using luminescence. The present invention also relates to a system, apparatus and method for successively testing blood to determine the compatibility of blood to different test substances using the luminescence as an indicator of the amount and/or activity of neutrophil in the blood.

BACKGROUND OF THE INVENTION

The immune system is an intricate collection of organs, tissues, cells and soluble factors that allow individuals to defend against harmful agents such as viruses, bacteria, fungi, parasitic organisms, and tumor cells. The immune system is a recognition system that distinguishes the body's own molecules from foreign molecules. When the immune system detects a foreign substance, called an antigen, it responds with a proliferation of cells that either attack the invader directly (the innate immune response) or produce specific defensive proteins called antibodies (the adaptive immune response). In contrast to the innate immune defences, which are always ready to fight a variety of infections, the adaptive immune response must be primed by the presence of an antigen, and the defensive cells and antibodies produced against the antigen are ineffective against any other foreign substance. Typically, the innate immune response has a rapid reaction time, whereas the adaptive immune response has a slow initiation and increases thereafter.

Allergies are hypersensitivities of the body's defence system to certain environmental antigens. Allergic reactions are typically very rapid and show extraordinary sensitivity to minute amounts of antigen. When antibodies that participate in allergenic reactions bind to antigens, a process called degranulation occurs in which the masked cells release a flood of histamine and other inflammatory mediators which cause some of the best recognized systems of allergy, namely sneezing, nasal irritation, itchiness of the skin and tearing of the eyes.

The presence of biologically active agents including antigens in a patient's body fluid, especially blood, has been determined using various techniques. One such technique entails the analysis of either bioluminescence or chemiluminescence for detecting the presence of a variety of luminescent analytes. For example, U.S. Pat. No. 5,445,794 discloses a luminescence measuring system comprising a luminometer designed for making bioluminescence and chemiluminescence measurements. The disclosed luminometer comprises a chamber into which a single test tube is received. The test tube once received in the chamber is held stationary while the chamber revolves around the test tube from the admission phase to the measurement phase and finally to the discharge phase. It is in the measurement phase that the reagent LUMIT is added to the sample and luminescence is measured. The disadvantage of the technique and apparatus disclosed in U.S. Pat. No. 5,445,794 is that it allows for only a single sample to move through the testing process from admission to discharge and as such, results in decreased efficiency and increased time in the overall testing process.

U.S. Pat. No. 6,335,166 discloses an automated analyser capable of performing multiple diagnostic assays simultaneously. The disclosed analyser includes a computer controller which runs analyser-controlling and assay-scheduling software to coordinate operation of the stations of the analyser and movement of each reaction receptacle through the analyser. The specimen pipette assembly of the disclosed analyser is coupled to a syringe pump which engages the specimen tubes carried on the specimen ring and which also engages pipette tips carried on a pipette wheel near the back portion of the specimen ring. The containers of the target capture reagent are carried on an inner rotable assembly constructed and arranged to selectively agitate the containers or present the containers for access by the probe of an automatic robotic pipette system. The reaction mixtures are prepared by the pipette system within each reaction receptacle. The contents of the reaction receptacle is subjected to magnetic separation wash procedures in the magnetic separation wash stations of the apparatus. The disclosed apparatus also contains a luminometer for detecting and/or quantifying the amount of light emitted by the contents of the reaction receptacle. The disclosed apparatus of U.S. Pat. No. 6,335,166 requires treatment of the contents of the reaction receptacle by magnetic separation wash procedures. Furthermore, the disclosed apparatus consists of several interconnected ring assemblies resulting in an overly complex and intricate apparatus.

Likewise, U.S. Pat. No. 3,617,222 discloses a complex apparatus and method for testing and classifying materials, which contain agglutinates. The method taught by U.S. Pat. No. 3,617,222 enables agglutinations to be detected either by nephelometry or by opacimetry and does not disclose a method for luminescence detection. The disclosed apparatus consists of an agitator comprising a turn-table subjected to motion around a circle in which the reaction mixture is introduced into the test vessel via two syringes. The first syringe is used to take small amounts of the sample, the second used to take into a small bottle a certain amount of liquid containing reagents, dilutant and flush water. A mass of liquid taken from the first and second syringes is directed into a probe which contains the sample of the reagent and dilutant, the contents of the probe being pushed into the reaction cups which are then subject to agitation. The apparatus taught in U.S. Pat. No. 3,617,222 discloses a two stage mixing procedure comprising a partial mixing in the probe and then a more complex mixing by agitation. Such a procedure disadvantageously results in an intricate preparation of the reaction mixture prior to the actual testing phase, thereby disadvantageously increasing the total time in the overall testing process.

U.S. Pat. No. 5,422,075 teaches a chemical luminescence-detection apparatus in which the chemical luminescence generated in a photometric cell is detected by an optical detector. The reagent used in the luminescent reaction is luminol. U.S. Pat. No. 5,422,075 also requires complex preparation of the sample prior to the testing phase and the luminescent reaction. The requisite preparation includes subjecting the reaction solution to several agitations and washes. Such a complex preparation of the sample disadvantageously increases the time required in the overall testing process.

SUMMARY OF THE INVENTION

Accordingly, it is an advantage of the present invention to provide an express-control system for analysing the compatibility of blood with other substances.

It is also an advantage of the present invention to provide an efficient system for blood testing using luminescence, which does not require complex preparation of the sample of blood prior to testing.

It is a further advantage of the present invention to provide a blood analyser which is able to test several substances concurrently or individually.

It is also an advantage of the present invention to provide a blood analyser, which is simple in design and easily disassembled for maintenance by the operator.

In one aspect, the present invention seeks to provide an efficient system for blood testing which is able to more efficiently and quickly test the compatibility of blood with various other substances without requiring complex preparation of the sample of blood prior to testing. Thereby, the present invention advantageously decreases the time required in the overall testing process by eliminating the expensive and time consuming steps associated with the complex preparation of the reaction mixture. The apparatus of the present invention is easy to use and advantageously facilitates easy maintenance by the user.

In another aspect, the present invention resides in a blood testing system for testing the compatibility of blood with different test substances, said system comprising: a displacement assembly comprising a plurality of canister holders, each canister holder adaptable to hold a canister, each canister initially containing a corresponding one of the test substances, said displacement assembly moving each of the plurality of canisters to a sampling stage, a reagent adding stage and an optical detector stage; a blood divider assembly at the sampling stage, said blood divider assembly operable to add a predetermined amount of the blood to each of the plurality of canisters containing the corresponding test substance as the canisters are moved to the sampling stage; a reagent divider assembly at the reagent adding stage, said reagent divider assembly operable to add a predetermined amount of luminescent reagent to each of the plurality of canisters as the canisters are moved to the reagent adding stage; an electro-optical multiplier assembly at the optical detector stage, the electro-optical multiplier assembly operable to measure luminescence of each of the plurality of canisters at a predetermined time period after the luminescent reagent has been added to the corresponding canister; and a central controller operable to control the functions of the drum assembly, the blood divider assembly, the reagent divider assembly and the electro-optical multiplier assembly and to process data received therefrom and assess the compatibility of the blood to each of the test substances.

In yet another aspect, the present invention resides in a blood analyser comprising: a displacement instrument, the displacement instrument comprising an admission site, a sample adding site, a reagent adding site and a discharge site; a plurality of canisters holders adaptable to hold a plurality of canisters, each canister initially containing a different test substance, wherein the plurality of canister holders are attached to the displacement instrument for movement from the admission site to the discharge site; a sample divider for supplying a predetermined amount of a blood sample to each of the plurality of canisters at the sample adding site; a reagent divider for supplying a predetermined amount of luminescent reagent to each of the plurality of canisters at the reagent adding site; a detection instrument for detecting luminescence after the luminescent reagent is added to each of the plurality of canisters; a converting instrument for converting the detected luminescence into a luminescence signal; and a central controller operable to control the functioning of the blood analyser and process data received from the blood analyser and assess the compatibility of the blood to each of the test substances.

In still another aspect, the present invention resides in a method for measuring the compatibility of blood with test substances using luminescence, the method comprising: adding a sample of blood to each of a plurality of canisters, each of the plurality of canisters containing a different test substance; adding a luminescent reagent to each of the plurality of canisters with the sample of blood and the test substance; subjecting the canisters to movement for a predetermined period of time until the canisters begin to luminescence; and detecting the amount of luminescence by a photometric measurement.

BRIEF DESCRIPTION OF THE DRAWINGS

Further aspects of the present invention will become apparent upon reading the following detailed description together with the accompanying drawings in which.

DETAILED DESCRIPTION OF THE PREFERRED EMBODIMENTS

Figure 1:
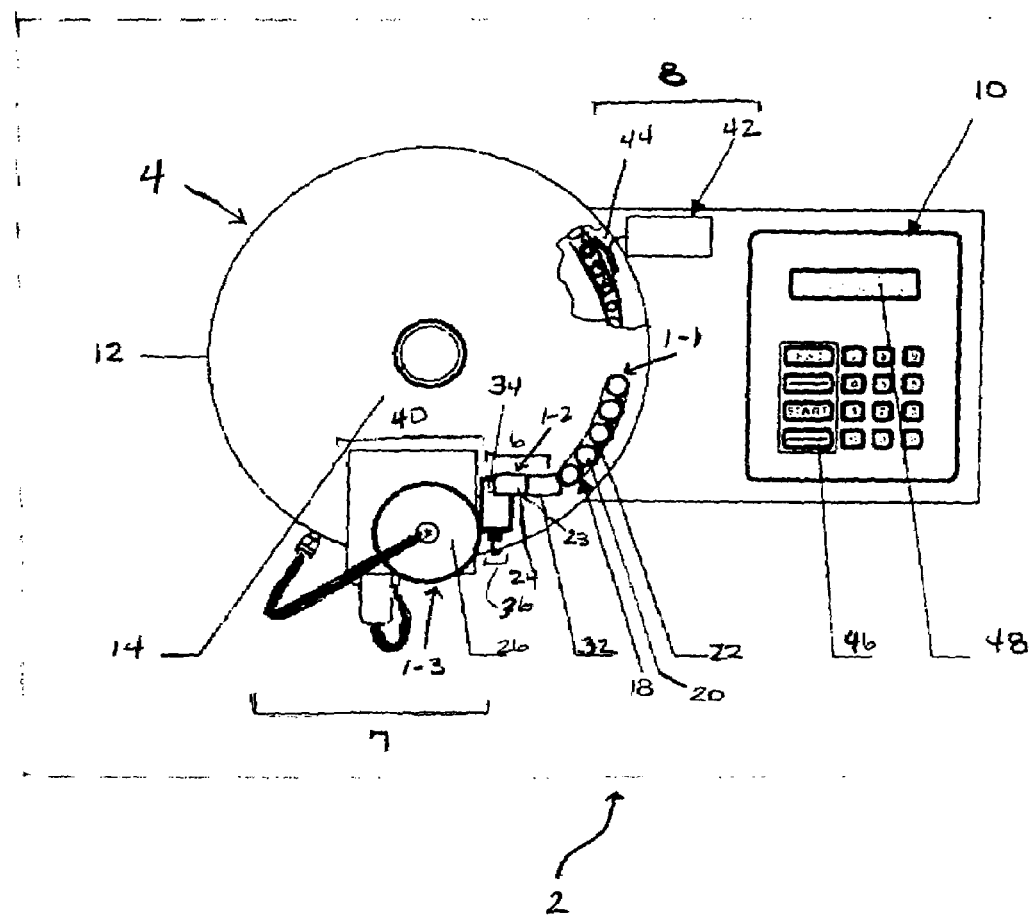
FIG. 1 is a top view of the blood testing system according to an embodiment of the present invention.

FIG. 1 is a top view of the blood testing system 2 according to a preferred embodiment of the present invention. The blood testing system 2 includes a displacement assembly 4, a blood divider assembly 6, a reagent divider assembly 7, an electro-optical multiplier assembly 8 and a central controller 10.

The displacement assembly 4 in one embodiment comprises a drum 12. The drum 12 includes a hollow cylindrical body with a circular base (not shown), a wall of constant circular cross-section (not shown) and a lid 14. The interior of drum 12 contains a plurality of canister holders 18. The canister holders 18 are adaptable to hold a plurality of canisters 20 each containing a test substance. In a preferred embodiment, the test substance in each of the plurality of canisters 20 can be one of a variety of different antigens. The lid 14 contains an opening 22 through which each of the plurality of canisters 20 can be inserted into the canister holders 18. Preferably the canisters 20 are test tubes with opaque walls. The displacement assembly 4 is operable to move each of the plurality of canisters 20 to an admission site 1-1, a sample adding site 1-2 in the sampling stage, a reagent adding site 1-3 in the reagent adding stage and a discharge site 1-4 (shown in FIG. 2) after an optical detection stage.

The plurality of the canisters 20 once inserted into the displacement assembly 4, at the admission site 1-1, are moved to the sampling site 1-2 where a sample of blood is added to each of the plurality of canisters 20 during the sampling stage.

At the sampling site 1-2, the blood divider assembly 6 includes a blood container 23, preferably a syringe, and canula 24 connectable to the blood container 23. The blood container 23 contains therein a sample of blood drawn from a subject and is operable to add a predetermined amount of the blood to a corresponding one of the plurality of canisters 20 containing the test substance. The blood divider assembly 6 further comprises a piston 34 coupled to the blood container 23 and canula 24, a piston connector 36 connecting the piston 34 to the central controller 10 and a blood divider sensor 32 operatively positioned adjacent the blood divider assembly 6, and coupled to the central controller 10. The blood divider sensor 32 is operable to detect the amount of blood dropped into each of the plurality of canisters 20, generate a blood sampling signal indicative thereof and send the blood sampling signal to the central controller 10. Movement of the piston 34 by the central controller 10 affects the release of a predetermined amount of blood from the blood container 23 and canula 24 into the corresponding canister of the plurality of canisters 20 containing the test substance. The dimension of the canula 23 is correlated to the amount the piston 34 must move in order to obtain the correct predetermined amount of blood in each of the plurality of canisters 20.

The plurality of canisters 20 are then moved to the reagent adding site 1-3 where a sample of reagent is added during the reagent adding stage.

At the reagent adding site, the reagent divider assembly 7 is operable to add a predetermined amount of the luminescent reagent to each of the plurality of canisters 20 containing both the test substance and the predetermined amount of blood. The reagent divider assembly 7 includes a reagent container 26 and an electro-pneumatic block assembly 40. The luminescent reagent, preferably Luminol, is held within the reagent container 26 while the electro-pneumatic block assembly 40 regulates the amount of reagent released from the reagent container 26 into each of the plurality of canisters 20.

After the amount of reagent is added to each of the plurality of canisters 20, the canisters 20 are moved to the optical detection stage.

At the optical detector stage, the electro-optical multiplier assembly 8 is electronically coupled to the drum 12 of the displacement assembly 4 and is operable to detect and measure photons or luminescence emanating from the plurality of canisters 20. The electro-optical multiplier assembly 8 comprises an electro-optical multiplier 42 and at least one photosensitive cathode 44. The electro-optical multiplier 42 transforms the luminescence detected by the at least one photosensitive cathode 44 into an electrical signal and transmits the electrical signal to the central controller 10.

The central controller 10 is operatively coupled to each of the displacement assembly 4, the blood divider assembly 6, the reagent divider assembly 7 and the electro-optical multiplier assembly 8. The central controller 10 is operable to control the functions of each of the aforementioned assemblies and is also operable to process data received therefrom and assess the compatibility of the blood to each of the test substances. The central controller 10 includes input ports (not shown), output ports (not shown), circuitry (not shown), a keypad 46 and an LCD display 48.

Figure 2:
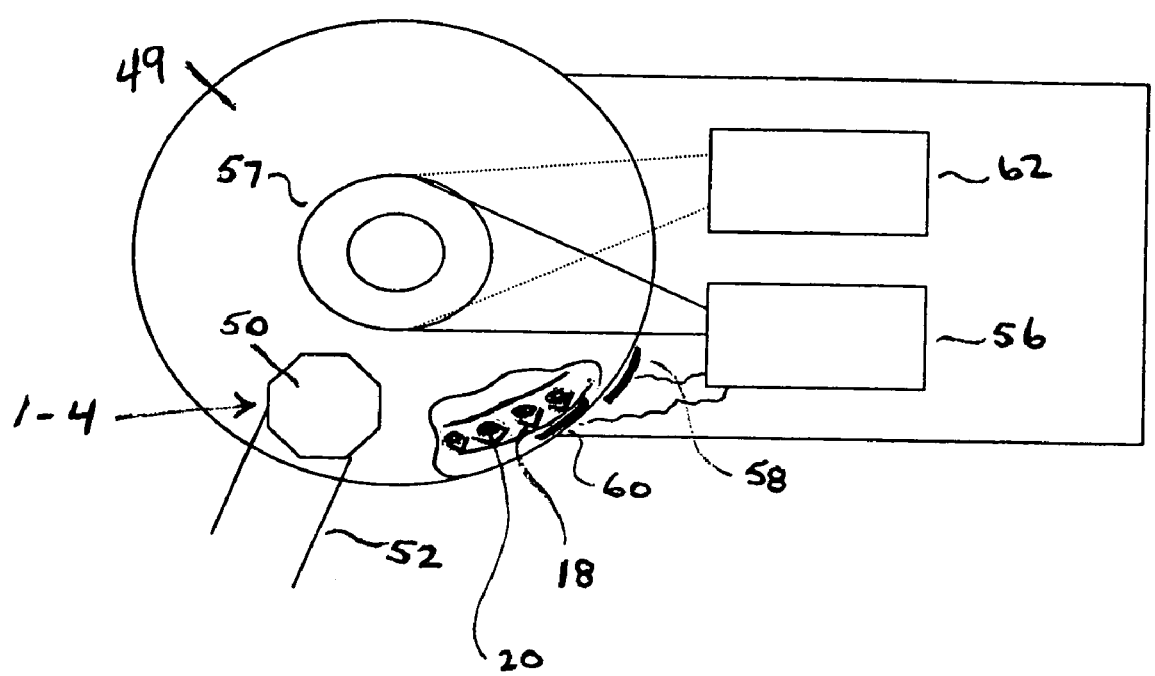
FIG. 2 is a bottom view of the blood testing system of FIG. 1 according to an embodiment of the present invention

Referring now to FIG. 2 a bottom view of the blood testing system 2 in accordance with an embodiment of the present invention is shown. A base 49 of the drum 12 contains a canister discharge opening 50 and a discharge mechanism 52 at the discharge site 1-4 operable to discharge the canisters from the displacement assembly after use. The discharge mechanism 52 is preferably a flexible hose adaptable to be directed to a waste container (not shown). The displacement assembly 4 further comprises a drum rotator 56 and a secondary drum rotator 62.

The drum rotator 56 is operable to rotate the drum from the admission site 1-1 through the sampling stage, the reagent adding stage and the optical detector stage to the discharge site 1-4. The drum rotor 56 is mechanically coupled to a drum flywheel 57. The drum rotor 56 is operable to rotate the drum flywheel 57 and thereby also rotate the drum 12. The drum rotor 56 also includes a first optical sensor 58 positioned adjacent to the drum 12 and which is operable to generate a drum positioning signal indicative of the rotation and the annular position of the drum 12 during rotation. The first optical sensor 58 is electronically coupled to the central controller 10 and sends the drum position signal to the central controller 10. The drum rotor 56 also comprises a second optical sensor 60 operatively positioned adjacent to the canister holders 18. The second optical sensor 60 is operable to generate a canister positioning signal indicative of the positioning of the canisters 20 within the drum 12 and to send the canister positioning signal to the central controller 10. The central controller 10 receives the drum positioning signal and the canister positioning signal and sends control signals to the displacement assembly 4 to control the displacement assembly 4.

The secondary drum rotator 62 is also coupled to drum 12. The secondary drum rotator 62 is operable to control friction of the drum 12 during rotation, and is also operable to prevent jamming of the plurality of canisters 20 contained therein. The secondary drum rotator 62 is also electronically coupled to the central controller 10, and is operable to receive the control signals therefrom. In response to the control signals received from the central controller 10, the secondary drum rotor 62 is able to adjust the rotation of the drum 12.

Figure 3:
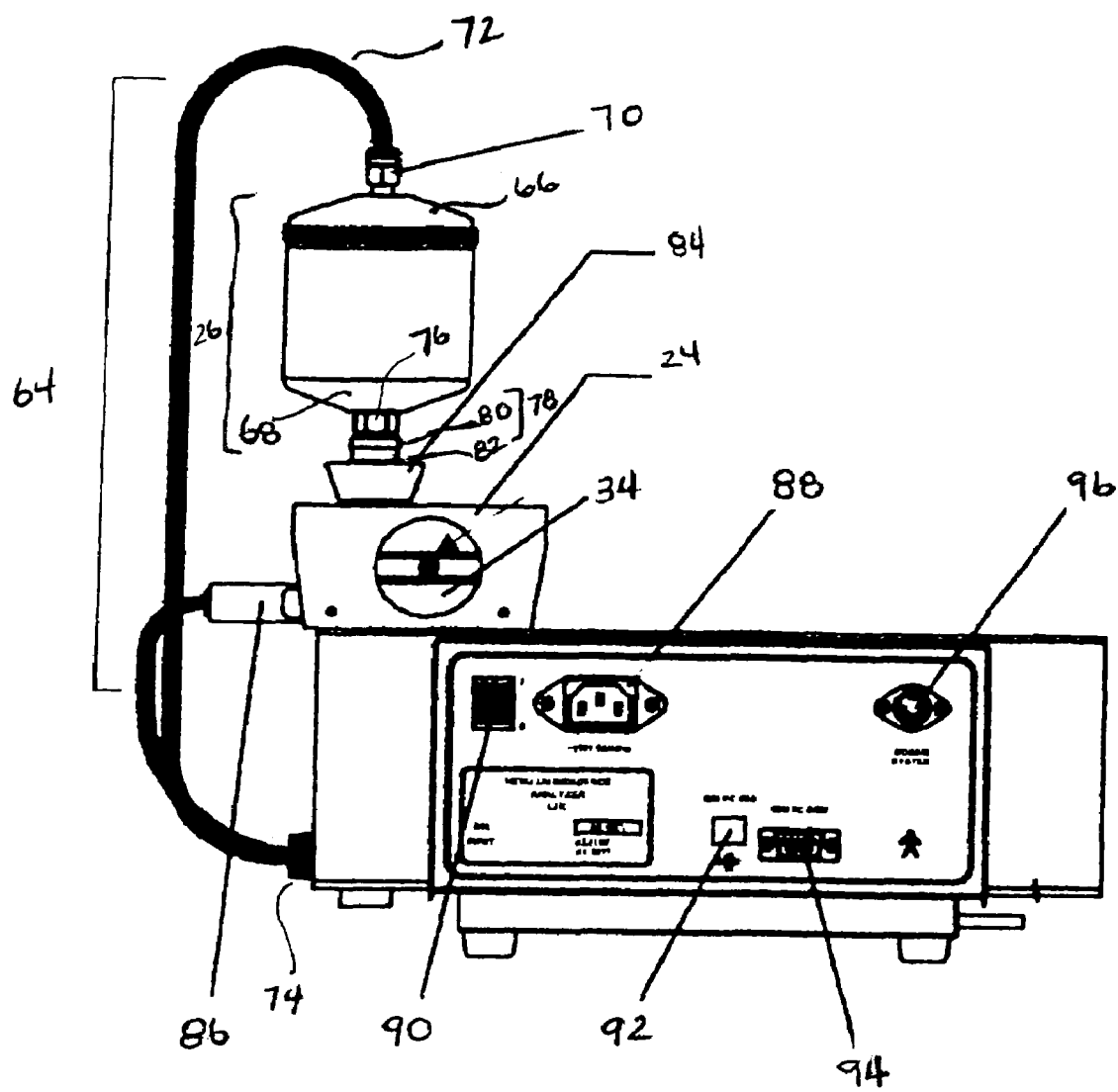
FIG. 3 is a side view of the blood testing system of FIG. 1 showing the connectors in accordance with a preferred embodiment of the invention.

FIG. 3 shows a side view of the blood testing system 2 of FIG. 1 in accordance with a preferred embodiment of the present invention. The reagent container 26 includes a top portion 66 and a bottom portion 68. The top portion 66 is removable to allow for the reagent container 26 to be filled with the luminescent reagent.

The reagent divider assembly 7 further comprises an electro-pneumatic block assembly 40, which is operable to regulate the amount of reagent released from the reagent container 26. The electro-pneumatic block assembly 40 includes an air compressor 74, a hose 72, a valve 78 and an electro-pneumatic block connector 86. The top portion 66 of the reagent container 26 contains a fitting 70 to which the hose 72 is attached. The hose 72 is also attached to the air compressor 74 to allow air to pass from the air compressor 74 into the reagent container 26. The bottom portion 68 of the reagent container 26 also contains a fitting 76 to which the valve 78 is attached on an inlet side 86 thereof. A disconnection safety cup 84, which is operable to prevent leakage from the electro-pneumatic valve 78 when not in use, is attached to an outlet side 82 of the valve 78. The outlet side 82 of the valve 78 is situated overhead of the plurality of canisters 20. The valve 78 is connected to the central controller 10 by the electro-pneumatic block connector 86. The valve 78 is operable to allow a predetermined amount of reagent to pass from the reagent container 26 into a corresponding one of the plurality of canisters 20.

A panel of the central controller is also shown including a power on/off switch 90, a USB PC connection Type B 92, a COM PC connection port 94, and a Blood-dozing system control connection port 96.

Figure 4:
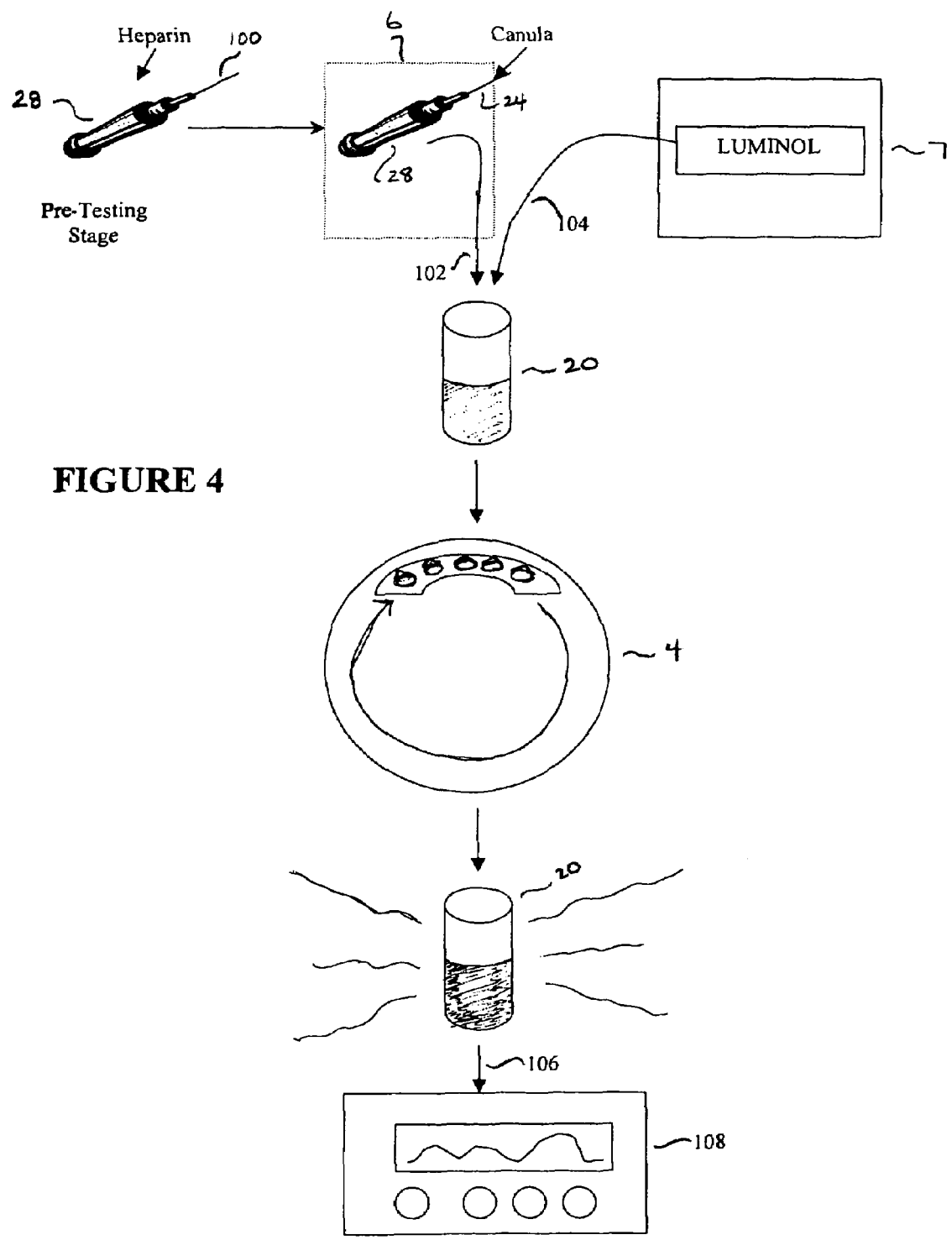
FIG. 4 is a flowchart diagram of a preferred method of operation of the blood testing system of FIG. 1 according to an embodiment of the invention.

Referring now to FIG. 4, a flowchart diagram of a preferred method of operation of the blood testing system 2 of FIG. 1, in accordance with an embodiment, is shown.

In a pre-testing stage a sample of blood is drawn from the subject into a syringe 28 and the needle 100. An anticoagulant, preferably heparin is also added to the sample of blood in the syringe 28. In a preferred embodiment the blood undergoes no further treatments, or washes other than the addition of the anticoagulant. The needle 100 of the syringe 28 is then replaced by the canula 24. The syringe 28 and canula 24 are then inserted into the blood divider assembly 6.

During the sampling stage 102 each of the plurality of canisters 20 pre-filled with the test substance, are moved into place beneath the blood divider assembly 6. A predetermined amount of blood, approximately two or three drops, is then added. During the next stage, the reagent adding stage 104, each of the plurality of canisters 20 with the test substance and the sample of blood are moved into place beneath the reagent divider assembly 7, where a predetermined amount of reagent, preferably Luminol, is added to the reaction mixture in each of the plurality of canisters 20. By way of non-limiting example, Luminol is added in an amount between 0 to 100 ml.

Each of the plurality of canisters 20 containing the test substance, blood, and Luminol are then moved for a predetermined period of time after which the canisters begin to luminese. In a preferred embodiment, the period of time which the canisters are moved corresponds approximately to the time taken for the displacement assembly 4 to move each of the plurality of canisters 20 from the reagent adding stage 104 to the optical detector stage 106. At the optical detector stage 106 the total luminescence is detected by the electro-optical multiplier assembly 8, converted into an electrical signal (a luminescence signal) and sent to the central controller 10. Thereafter each of the plurality of canisters 20 are successively ejected from the displacement assembly 4 into a waste receptacle (not shown).

The luminescence signal generated by the electro-optical multiplier 42, once received in the central controller 10 is processed in a measurement stage 108. During the measurement stage 108 the received information is analysed through a software program designed to measure the luminosity as an indicator of at least one of the presence and activity of neutrophil in the blood and more specifically the granulacy of the blood. While it has been disclosed that the presence and activity of neutrophil in the blood is measured, a skilled artisan could envision alternate embodiments that are possible utilising the present invention as for example, the presence of Eosinophil in the blood.

Although it has been described in the preferred embodiment that the sampling stage 102 and the reagent adding stage 104 occur separately, it is to be understood that this is but one embodiment of the invention. A skilled artisan would readily appreciate that the sampling stage 102 and reagent adding stage 104 could occur concurrently to achieve the objects of the present invention.

Figure 5:
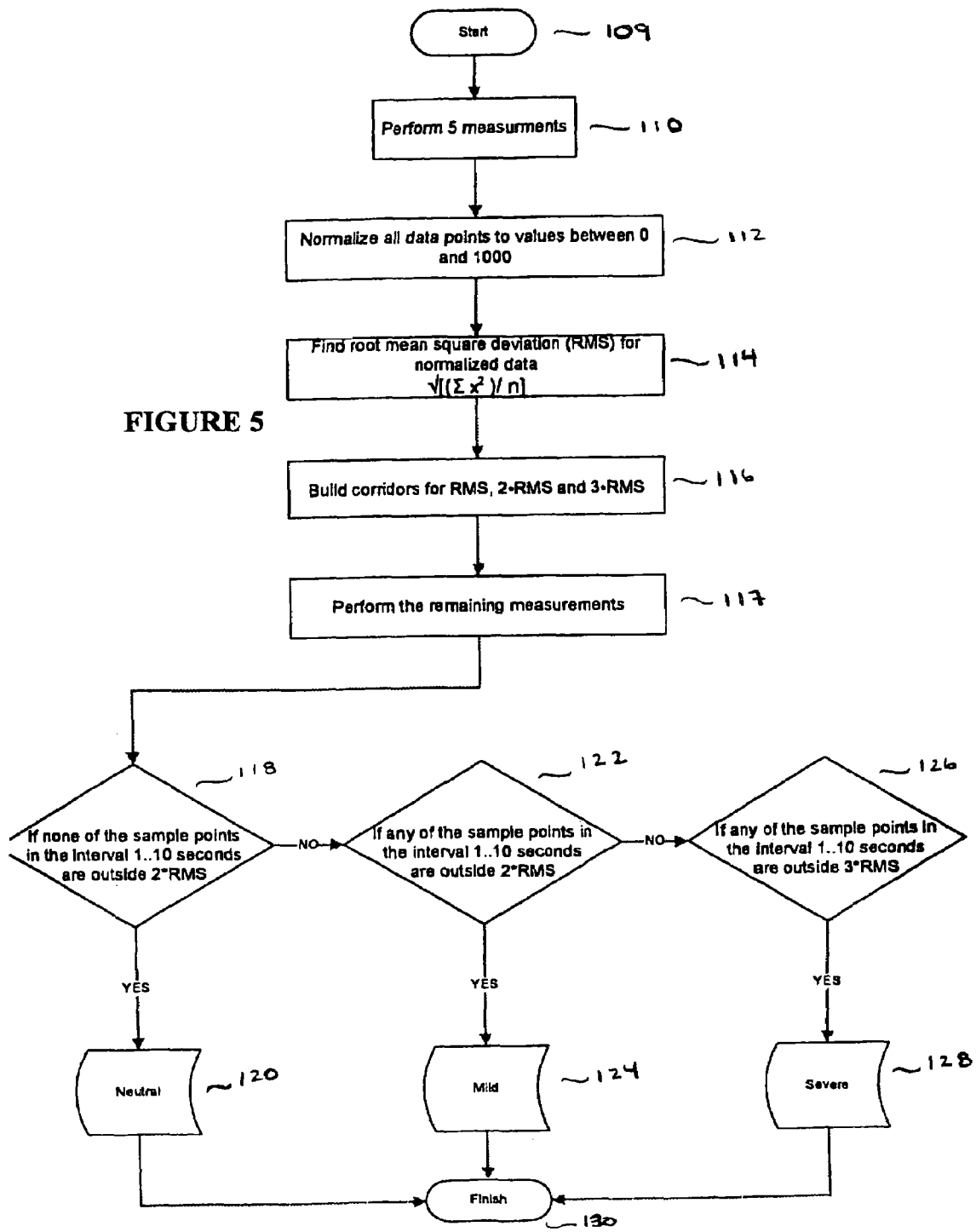
FIG. 5 is an algorithm of a preferred mode of operation of the blood testing system of FIG. 1 according to an embodiment of the invention.

Referring now to FIG. 5 an algorithm is shown for a preferred mode of operation of the blood testing system 2 of FIG. 1 according to an embodiment of the invention.

The central controller 10 processes data received from the various assemblies of the system 2 to assess the compatibility of the blood to each of the test substances. The central controller 10 receives the luminescence signal for each of the plurality of canisters 20, correlates the signal to the corresponding test substance and generates a compatibility output for each of the test substances based on the luminescence signal.

After the blood testing system starts 109 it performs five measurements 110 generating data which is then normalized to values between 0 and 1000 at operation 112. Thereafter the root mean square deviation (RMS) for the normalized data is calculated according to the formula $\sqrt{[(\Sigma x^2)/n]}$ at operation 114. Corridors are built for the values RMS, 2*RMS and 3*RMS at operation 116. Thereafter the remaining measurements are performed at operation 117. If none of the sample points in the interval 1 . . . 10 seconds are outside 2*RMS at operation 118, then the reading is "Neutral" at operation 120 and the system proceeds to the "Finish" operation 130. If any of the sample points in the interval 1 . . . 10 seconds are outside 2*RMS at operation 122 then the reading is "Mild" at operation 124 and the system proceeds to the "Finish" operation 130. If any of the sample points in the interval 1 . . . 10 seconds are outside 3*RMS at operation 126 then the reading is "Severe" at operation 128 and the system proceeds to the "Finish" operation 130. The aforementioned measurements of "Neutral", "Mild" and "Severe" relate to the level of compatibility of the blood to the specific antigen.

Accordingly, in one embodiment, the luminescence signal comprises at least 3 luminescence sample measurements for each of the plurality of canisters, and, the central controller generates the compatibility output for each of the test substances by determining a root mean square deviation of each of the at least 3 measurements and generating a neutral output for the test substance if none of the sample measurements are outside of two times the root mean square, generating a mild output for the test substance if at least one of the sample measurements are outside of two times the root mean square, and, generating a severe output for the test substance if at least one of the sample measurements is outside of three times the root mean square.

In another embodiment, the luminescence signal comprises at least 5 luminescence sample measurements for each test sample, and, the electro-optical multiplier acquires the at least 5 sample measurements for each of the plurality of canisters within 5 to 15 seconds.

In yet another embodiment, the central controller outputs one of the neutral output, the mild output and the severe output for each of the test substances indicating the compatibility of the blood to each of the test substances in the plurality of canisters.

It is to be understood that all the various features of the invention have been described with respect to one or another of the embodiments in the invention, and that the various features and embodiments of the invention may be combined or used in combination with other features and embodiments of the invention as described and illustrated herein.

Furthermore although this disclosure has been described and illustrated as containing preferred embodiments of the invention, it is to be understood that the invention is not restricted to these particular embodiments. Rather, the invention includes all embodiments, which are functional, electrical, electronical or mechanical equivalents of the specific embodiments and features that have been described herein. It is also to be understood that other types of testing could be achieved through utilizing the system, method and apparatus of the present invention, as for example blood compatibility with tissue cells from transplanted organs.

The embodiments of the invention in which an exclusive property or privilege is claimed are defined as follows:

1. A blood testing system for testing the compatibility of blood with different test substances, said system comprising:
   a plurality of canisters initially containing a corresponding one of the test substances;
   a plurality of canister holders, each canister holder to hold a single canister;
   a displacement assembly comprising a drum housing the plurality of canister holders, said displacement assembly moving each of the plurality of canisters to a sampling stage, a reagent adding stage, and an optical detector stage;
   a blood divider assembly at the sampling stage, said blood divider assembly configured to add a predetermined amount of the blood to each of the plurality of canisters containing the corresponding test substances as the canisters are moved to the sampling stage;

a reagent divider assembly at the reagent adding stage, said reagent divider assembly configured to add a predetermined amount of luminescent reagent to each of the plurality of canisters as the canisters are moved to the reagent adding stage;

an electro-optical multiplier assembly at the optical detector stage, the electro-optical multiplier assembly configured to measure luminescence of each of the plurality of canisters at a predetermined time period after the luminescent reagent has been added to the corresponding canister;

a central controller configured to control the functions of the displacement assembly, the blood divider assembly, the reagent divider assembly and the electro-optical multiplier assembly and to process data received therefrom and assess the compatibility of the blood to each of the test substances;

the electro-optical multiplier assembly comprises an electro-optical multiplier, and at least one photosensitive cathode wherein the photosensitive cathode detects luminescence in the optical detector stage, and wherein the electro-optical multiplier transforms the luminescence detected by the photosensitive cathode into a luminescence signal and transmits the luminescence signal to the central controller;

a display;

the central controller processes the data to assess the compatibility of blood to each of the test substances by receiving the luminescence signal for each of the plurality of canisters, correlates the luminescence signal to the corresponding test substance and generates a compatibility output on the display for each test substance based on the luminescence signal; and the luminescence signal comprises at least 3 luminescence sample measurements for each of the plurality of canisters, and, the central controller generating the compatibility output for each of the test substances by determining a root mean square deviation of each of the at least 3 measurements and generating a neutral compatibility output for the test substance if none of the sample measurements are outside of two times the root mean square, generating a mild compatibility output for the test substance if at least one of the sample measurements are outside of two times the root mean square, and generating a severe incompatibility output for the test substance if at least one of the sample measurements is outside of three times the root mean square;

wherein the drum is in cooperative engagement with the blood divider, the reagent divider, and the electro-optical multiplier assembly.

2. The system according to claim 1 wherein the displacement assembly further comprises:
a drum rotator mechanically coupled to the drum and the central controller, wherein the drum rotator is configured to rotate the drum;
a first optical sensor operatively positioned adjacent the drum, the first optical sensor generating a drum position signal indicative of rotation of the drum and annular positioning of the drum during rotation; and
a second optical sensor operatively positioned adjacent the canister holders, the second optical sensor generating a canister position signal indicative of the positioning of the canisters contained within the drum,
wherein the central controller receives the drum position signal and the canister position signal and sends control signals to the displacement assembly to control the displacement assembly.

3. The system according to claim 2 wherein the displacement assembly further comprises a secondary drum rotor configured to control friction of the drum during rotation thereof and operable to prevent jamming of the canisters contained therein, in response to the control signals received from the controller.

4. The system according to claim 1 wherein the blood divider assembly comprises: a blood container containing a sample of blood; and
a cannula connectable to the blood container, the cannula configured to allow the predetermined amount of blood to pass therethrough into a corresponding canister of the plurality of canisters.

5. The system according to claim 4, wherein the blood divider assembly further comprises:
a piston coupled to the blood container;
a piston connector connecting the piston to the central controller;
a blood divider sensor operatively positioned adjacent the blood divider assembly and coupled to the central controller, the blood divider sensor generating a blood sampling signal indicative of the amount of blood dropped into each of the plurality canisters; and
the central controller receives the blood sampling signal and in response thereto effects movement of the piston to control release of the predetermined amount of blood from the blood container into the corresponding canister of the plurality of canisters.

6. The system according to claim 4 wherein the blood container is a syringe.

7. The system according to claim 1 wherein the reagent divider assembly comprises: a reagent container within which the luminescent reagent is held; and an electro-pneumatic block assembly operable to regulate the amount of reagent released from the reagent container into each of the plurality of canisters.

8. The system according to claim 7, wherein the reagent container includes a top portion and a bottom portion and wherein the electro-pneumatic block assembly further comprises:
an air compressor;
an electro-pneumatic valve connected to the bottom portion of the reagent container, wherein the valve allows the predetermined amount of reagent to pass from the reagent container into each of the plurality of canisters;
a hose connected at a first end thereof to the air compressor and connected at a second end thereof to the top portion of the reagent container, the hose configured to allow air to pass from the air compressor into the reagent container; and
an electro-pneumatic block connector operable to connect the electro-pneumatic valve to the central controller.

9. The system according to claim 8 wherein the valve comprises an inlet side, an outlet side and a disconnection safety cup, wherein the inlet side is connectable to the bottom portion of the reagent container, wherein the outlet side is situated overhead of the canisters; and
wherein the disconnection safety cup is connectable to the outlet side of the electro-pneumatic, the disconnection safety cup configured to prevent leakage of the reagent from the electro-pneumatic valve.

10. The system according to claim 1, wherein the luminescence reagent is Luminol.

11. The system according to claim 10, wherein the predetermined amount of the Luminol reagent added is in the range of 0.01 to 100 ml.

12. The system according to claim 1 wherein the test substance is an antigen.

13. The system according to claim 1 wherein at least one of the activity and presence of neutrophil is measured by the amount of luminescence.

14. The system according to claim 1 wherein the electro-optical multiplier acquires the at least 3 sample measurements for each of the plurality of canisters within 5 to 15 seconds.

15. The system according to claim 14 wherein the central controller outputs one of the neutral output, the mild output and the severe output for each of the test substances indicating the compatibility of the blood to each of the test substances in the plurality of canisters.

* * * * *